United States Patent
Arellano et al.

(10) Patent No.: US 9,228,941 B2
(45) Date of Patent: Jan. 5, 2016

(54) COMBUSTOR IMAGING INSPECTION SYSTEM

(71) Applicant: Solar Turbines Incorporated, San Diego, CA (US)

(72) Inventors: Leonel Arellano, Poway, CA (US); Nathaniel David Brown, Encinitas, CA (US)

(73) Assignee: Solar Turbines Incorporated, San Diego, CA (US)

( * ) Notice: Subject to any disclaimer, the term of this patent is extended or adjusted under 35 U.S.C. 154(b) by 368 days.

(21) Appl. No.: 13/671,300

(22) Filed: Nov. 7, 2012

(65) Prior Publication Data
US 2014/0125791 A1    May 8, 2014

(51) Int. Cl.
*H04N 7/18*    (2006.01)
*G01N 21/47*   (2006.01)
*H04N 5/225*   (2006.01)

(52) U.S. Cl.
CPC ........ *G01N 21/47* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 5,255,096 | A * | 10/1993 | Boyle | 348/95 |
| 6,525,500 | B2 | 2/2003 | Hatley et al. | |
| 6,532,840 | B2 * | 3/2003 | Hatley et al. | 73/866.5 |
| 7,271,894 | B2 * | 9/2007 | Devitt et al. | 356/241.1 |
| 2012/0169326 | A1 * | 7/2012 | Krishna et al. | 324/240 |
| 2012/0281084 | A1 * | 11/2012 | Hatcher et al. | 348/83 |
| 2014/0053568 | A1 * | 2/2014 | Hatcher et al. | 60/773 |

OTHER PUBLICATIONS

Brown et al. "Inspect da Gadget." Department of Mechanical and Aerospace Engineering and Jacobs School of Engineering at University of California San Diego. UCSD Senior Project Poster, Jun. 2009, 1 page.

* cited by examiner

*Primary Examiner* — Kate Luo
(74) *Attorney, Agent, or Firm* — Procopio, Cory, Hargreaves & Savitch LLP (57) ABSTRACT

An imaging inspection system and inspection method for a combustion chamber of a gas turbine engine having an imaging inspection device and a controller. The imaging inspection device includes a combustor interface, an inspection head having a first camera, an inspection head extender, a roll actuator, and a pitch actuator. The controller is configured to manipulate the inspection head in a predefined sequence.

19 Claims, 5 Drawing Sheets

COMBUSTOR IMAGING INSPECTION SYSTEM

TECHNICAL FIELD

The present disclosure generally pertains to gas turbine engines, and is more particularly directed toward an imaging inspection system for a combustor of a gas turbine engine.

BACKGROUND

High performance gas turbine engines typically rely on increasing turbine inlet temperatures to increase both fuel economy and overall power ratings. These higher temperatures, if not compensated for, oxidize engine components and decrease component life. Components of the gas turbine, particularly the combustor are periodically inspected visually. Currently, manual boroscopes or actuated inspection heads are operated for combustor inspections.

U.S. Pat. No. 7,271,894 issued to Devitt et al. on Apr. 6, 2010 shows an imaging system for robotically inspecting gas turbine combustion components. In particular, the disclosure of Devitt et al. is directed toward a system for in situ inspection of a surface of a hot gas component of a turbine. The system includes a robot having an elongated inspection arm extending toward the surface of the hot gas component; and an inspection head carried adjacent an end of the inspection arm remote from controls for the robot. The inspection head is manipulated by the inspection arm to locate the inspection head adjacent interior wall portions defining the hot gas component including by displacing the inspection head in a generally axial direction and generally radially toward a wall portion of the hot gas component being inspected. The inspection head is configured with a UV system to excite and detect fluorescence from a taggant material disposed in a coating on the hot gas component.

The present disclosure is directed toward overcoming known problems and/or problems discovered by the inventors.

SUMMARY OF THE DISCLOSURE

An imaging inspection system and inspection method for a combustion chamber of a gas turbine engine is disclosed herein. The imaging inspection system having an imaging inspection device and a controller. The imaging inspection device includes a combustor interface, an inspection head having a first camera, an inspection head extender, and actuators to control the spatial position of the imaging inspection device (don't want to limit to two actuators). The controller is configured to manipulate the inspection head in a predefined sequence. According to one embodiment, a method for inspecting a combustion chamber of a gas turbine engine is also disclosed herein. The method includes securing an imaging inspection device to an injector port, initiating an automated sequence of manipulations of the imaging inspection device via a controller, recording data obtained via the automated sequence of manipulations of the imaging inspection device, and removing the imaging inspection device from the injector port.

DETAILED DESCRIPTION

The combustor imaging inspection system is an automated inspection camera (with supporting hardware and software) used to inspect the inner surface of a gas turbine combustion chamber. The combustor imaging inspection system may be used to determine the overall health of the lining of the combustion chamber. Where damage is present, the combustor imaging inspection system may be used to identify the extent of the damage, the location of the damage, and the type of damage it is.

Figure 1:
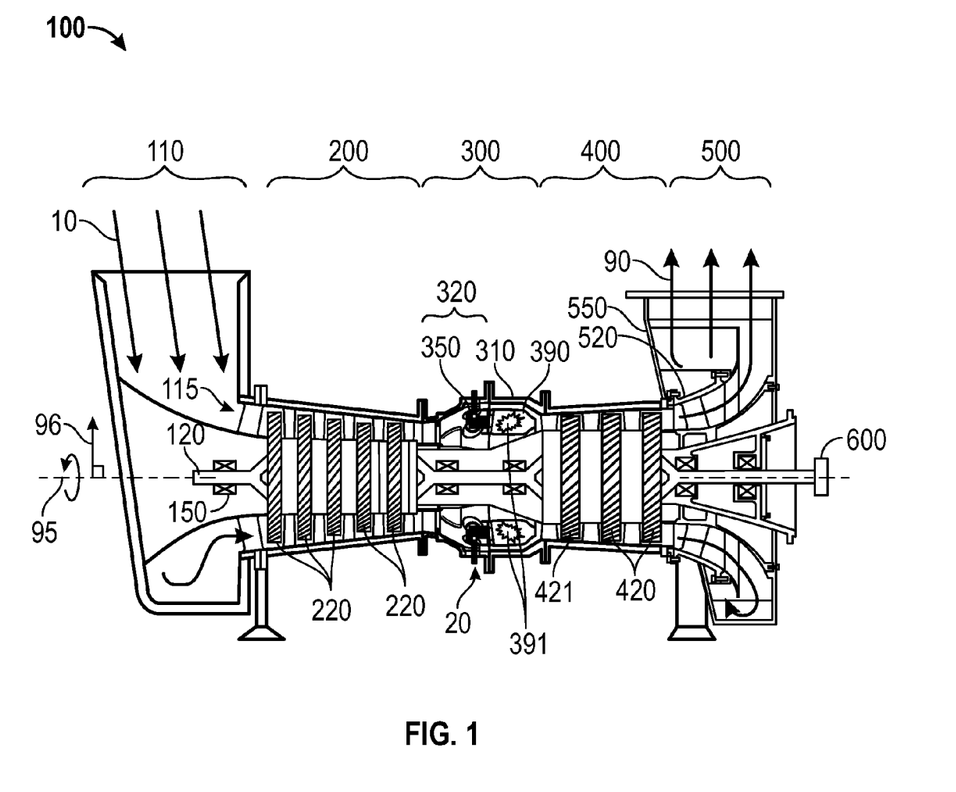
FIG. 1 is a schematic illustration of an exemplary gas turbine engine.

FIG. 1 is a schematic illustration of an exemplary gas turbine engine. Some of the surfaces have been left out or exaggerated (here and in other figures) for clarity and ease of explanation. Also, the disclosure may reference a forward and an aft direction. Generally, all references to "forward" and "aft" are associated with the flow direction of primary air (i.e., air used in the combustion process), unless specified otherwise. For example, forward is "upstream" relative to primary air flow, and aft is "downstream" relative to primary air flow.

In addition, the disclosure may generally reference a center axis 95 of rotation of the gas turbine engine, which may be generally defined by the longitudinal axis of its shaft 120 (supported by a plurality of bearing assemblies 150). The center axis 95 may be common to or shared with various other engine concentric components. All references to radial, axial, and circumferential directions and measures refer to center axis 95, unless specified otherwise, and terms such as "inner" and "outer" generally indicate a lesser or greater radial distance from, wherein a radial 96 may be in any direction perpendicular and radiating outward from center axis 95.

Structurally, a gas turbine engine 100 includes an inlet 110, a gas producer or "compressor" 200, a combustor 300, a turbine 400, an exhaust 500, and a power output coupling 600. One or more of the rotating components are coupled by one or more shafts 120. The compressor 200 includes one or more compressor rotor assemblies 220. The turbine 400 includes one or more turbine rotor assemblies 420. The exhaust 500 includes an exhaust diffuser 520 and an exhaust collector 550.

As illustrated, the combustor 300 includes a combustor case 310, a diffuser 320, an injector 350 and a combustion chamber 390. Depending on its configuration, the combustor 300 may include one or more of these components. For example, combustor 300 may include a plurality of injectors 350 annularly distributed around the center axis 95. For clarity and illustration purposes, only one injector 350 is shown here in the installed position.

The combustor 300 may be generally configured as a can, annular, or cannular type, depending on the configuration of its combustion chamber(s) 390. Here, combustor 300 is configured as an annular combustor. In particular, the combustion chamber 390 has a continuous liner and casing in a ring (the annulus). Accordingly, the plurality of injectors 350 are distributed around the annulus.

Functionally, a gas (typically air 10) enters the inlet 110 as a "working fluid", and is compressed by the compressor 200.

In the compressor 200, the working fluid is compressed in an annular flow path 115 by the series of compressor rotor assemblies 220. In particular, the air 10 is compressed in numbered "stages", the stages being associated with each compressor rotor assembly 220. For example, "4th stage air" may be associated with the 4th compressor rotor assembly 220 in the downstream or "aft" direction—going from the inlet 110 towards the exhaust 500). Likewise, each turbine rotor assembly 420 may be associated with a numbered stage. For example, first stage turbine rotor assembly 421 is the forward most of the turbine rotor assemblies 420. However, other numbering/naming conventions may also be used.

Once compressed air 10 leaves the compressor 200, it enters the diffuser 320 and combustor 300, where it is diffused and fuel 20 is added. Air 10 and fuel 20 are injected into the combustion chamber 390 via injector 350 and ignited in the combustion region 391 throughout the annulus. After the combustion reaction, energy is then extracted from the combusted fuel/air mixture via the turbine 400 by each stage of the series of turbine rotor assemblies 420. Exhaust gas 90 may then be diffused in exhaust diffuser 520 and collected, redirected, and exit the system via an exhaust collector 550. Exhaust gas 90 may also be further processed (e.g., to reduce harmful emissions, and/or to recover heat from the exhaust gas 90).

One or more of the above components (or their subcomponents) may be made from stainless steel and/or durable, high temperature materials known as "superalloys". A superalloy, or high-performance alloy, is an alloy that exhibits excellent mechanical strength and creep resistance at high temperatures, good surface stability, and corrosion and oxidation resistance. Superalloys may include materials such as HASTELLOY, INCONEL, WASPALOY, RENE alloys, HAYNES alloys, INCOLOY, MP98T, TMS alloys, and CMSX single crystal alloys.

Figure 2:
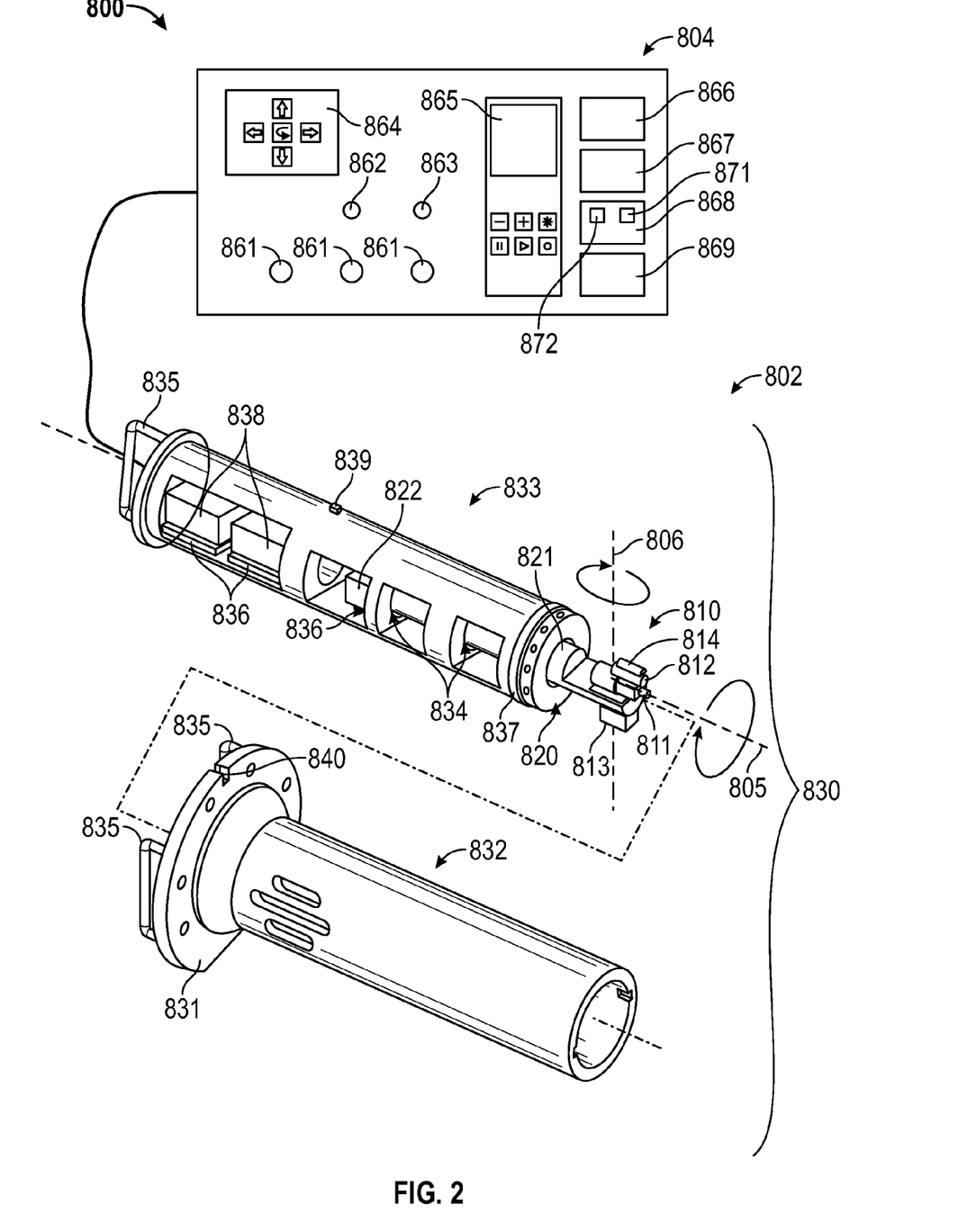
FIG. 2 shows an exemplary imaging inspection system as a partially exploded isometric view of an exemplary imaging inspection device and a schematic illustration of an exemplary controller.
Figure 4:
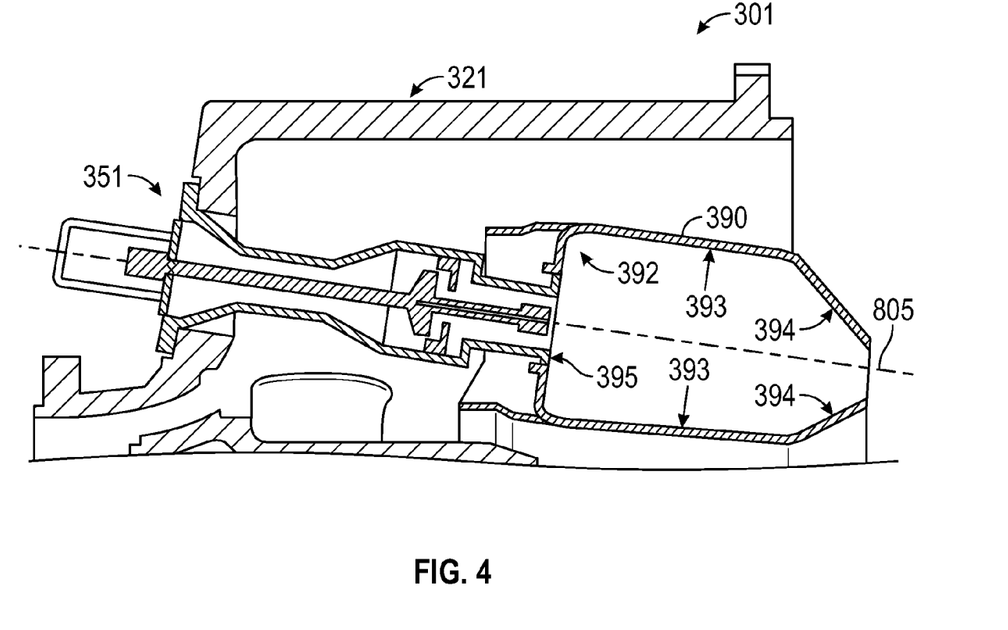
FIG. 4 is partial cutaway view of a 180-degree injector installed in a combustion chamber of a gas turbine engine.

FIG. 2 is a partially exploded isometric view of an exemplary imaging inspection device and a schematic illustration of an exemplary controller. In particular, the imaging inspection system 800 is an automated inspection camera (with supporting hardware and software) configured to inspect the inner surface of the combustion chamber 390 of FIG. 1. FIG. 2 is partially exploded to better illustrate components of the imaging inspection system 800. The imaging inspection system 800 includes an imaging inspection device 802 and a controller 804. The imaging inspection device 802 is configured to be installed into and inspect one or more combustion chambers such as combustion chamber 390 (FIG. 4). The imaging inspection device 802 may have a primary axis 805, which, for convenience, may refer to an axis of insertion into the combustion chamber 390.

The imaging inspection device 802 includes an inspection head 810, an inspection head extender 820, and an inspection device housing 830. The inspection head 810 is configured to perform the inspection of the combustion chamber 390. The inspection head 810 may include a camera 811, a light source 812, a pitch actuator 813, and a sensor 814. The inspection head may be articulable and may include additional components such as landing areas, mounting brackets, actuators, and other ancillary devices.

The camera 811 is configured to take images of the inner surface of the combustion chamber 390. The camera 811 may be a video and/or a still camera. According to one embodiment, the camera's optics may reside on the inspection head 810 while other camera components may reside off the inspection head 810, for example in the inner platform 833.

According to one embodiment, the inspection head 810 includes a plurality of cameras 811 (or camera optics), wherein the cameras 811 are still, video, non-visible light (e.g., UV for inspecting thermal barrier coating TBC), or any combination thereof. Moreover, with a plurality of cameras 811, the cameras 811 may be further configured for advanced imaging options such as 3-D mapping, creating ocular views, including multi-view/focus images, rapid imaging of multiple regions simultaneously, etc. Upon recording or receiving images, the camera 811 communicates the images or stores them locally, for example in a local memory card. According to one embodiment, the camera 811 may be the POV 1.5, manufactured by V.I.O., Inc. of Marquette, Mich., in which case, certain functionality described herein may be shared, and other functionality distributed across the imaging inspection system 800.

According to one embodiment, the camera 811 may include zoom capability. For example, the camera 811 may be configured to vary its focal distance, both to zoom in and out. This feature may be coordinated such that, where the inspection head extender 820 has a fixed length, focus and/or image resolution may remain constant despite varying lengths between the camera 811 and the liner of combustion chamber 390. Additionally, the camera 811 may zoom closer to areas of interest during the inspection.

According to one embodiment, the camera 811 may be small, measuring on the order of 1" (2.54 cm) at its widest diameter, and approximately 2.5" (6.35 cm) in length. The camera 811 may produce DVD quality video, with a resolution of 720×480 pixels and a frame rate of 30 frames per second. The camera 811 may have a field of vision is approximately 110-degrees. The camera 811 may also be waterproof, dustproof, and shock-resistant, with an operating temperature of −40 deg. F. to 185 deg. F. (−40 deg. C. to 85 deg. C.). The camera 811 may be battery powered, for example, by standard AA batteries. Alternately, the camera 811 may have other specification as convenient or beneficial.

According to one embodiment, the camera 811 may be controlled by a built-in and/or tethered video recorder, which records all video straight onto an SD card. The video recorder and memory may be implemented, for example, remotely from the inspection head 810, for example in controller 804. The camera 811 may also include a small microphone built into the tether. This microphone may provide an opportunity for even more detailed inspections, as an inspector will be able to records comments to the video. In addition the tethered camera 811 may include imaging software that allows for simple video editing. For example, the imaging software may include a "tagging" feature that allows the inspector to "tag" the clip at certain points of interest. Tags may include any information of interest such as merely the "tag" itself, biographical information (e.g., serial number, engine model, date/time), etc.

The light source 812 is configured to illuminate the inner surface of the combustion chamber 390. In particular, the light source 812 illuminates areas of the combustion chamber 390 to be recorded by the camera 811. According to one embodiment, the imaging inspection device 802 may include a plurality of the light sources 812, which may reside on and/or off the inspection head 810. The light source 812 may emit visible light or a specialized light, and/or UV light or other non-visible electromagnetic radiation.

The light source 812 may be fixed on the inspection head 810 and/or near the camera 811 or on the camera 811. Alternately, the light source 812 may be located at a remote location. For example, according to one embodiment, the light source 812 may be located on the inspection device housing 830 or the inspection head extender 820 to provide indirect and/or ambient lighting. The light source 812 may take a form factor that facilitates its mounting. For example, when located on the inspection device housing 830, the light source 812 take the form of a light strip or other distributed lighting configuration.

According to one embodiment, the light source 812 may include LED lights. The light source 812 may include a combination of rigid bars of warm white light and flexible ribbons of cool white light LED's. For example, the light source 812 may be LED lights produced by JKL Components Corporation of Pacoima, California. The light source 812 may be configured to produce ambient lighting rather then direct lighting. These lights may be placed on the both the outside of the inspection device housing 830 and on the inspection head 810.

The pitch actuator 813 is configured to manipulate the camera 811 about a transverse axis to the primary axis 805, or its pitch axis 806. In particular, the pitch actuator 813 controls rotational motion of the camera generally sweeping between an upstream view and a downstream view. For example, the pitch actuator 813 may have a 180-degree field of sweep beginning approximately at its insertion point and terminating approximately at its insertion direction.

The pitch actuator 813 may be mechanically coupled to an extension arm 821 and the camera 811. The pitch actuator 813 may also be mechanically coupled to light source 812, which may be via the camera 811. In addition, the pitch actuator 813 may work in coordination with any other actuators of the imaging inspection device 802 to position and orient the camera 811 as needed to perform the inspection of the combustion chamber 390.

According to one embodiment, the pitch actuator 813 may be a stepper motor. For example, the pitch actuator 813 may have a basic step angle of 0.72°, for a total of 500 steps per revolution. In addition, the pitch actuator 813 may be small or fitting within a (0.79"×0.98"×1.52" (2 cm×2.5 cm×3.85 cm) envelope. The 1.52" (3.85 cm) length may include the motor shaft. As with all components entering the combustion chamber 390, there should be no contact with the inner walls of the combustion chamber 390. According to one embodiment, the pitch actuator 813 may be a model CRK513PAP stepper motor from Oriental Motor of Torrance, Calif. Alternately, one or more differently configured actuators may be used to provide maneuverability to the camera 811 to conduct inspections as discussed below.

According to one embodiment, the imaging inspection device 802 may include one or more sensors 814 located on or about the inspection head 810. In particular, the sensor 814 may measure or otherwise provide feedback as to the conditions of the combustion chamber 390 or the inspection. For example, the sensor 814 may be a proximity sensor or a displacement sensor. The sensor 814 may be configured to measure the actual location of the inner wall (or liner) of the combustion chamber 390. The sensor 814 may be configured to provide data that can be used to determine differences between the actual location of the inner wall (or liner) of the combustion chamber 390 from its design location (e.g., identifying damage, wear, etc.), and/or measuring any distortion of the liner of the combustion chamber 390. The sensor 814 may be configured to provide for a "HOME" position to return to prior to an inspection, for example, using location information. In addition, the sensor 814 may be side-by-side, or otherwise coordinated with the camera 811. This coordination may be used to avoid wall contact during inspections, measure distortion or surface features, and/or create specialized inspection maps (3-D, ocular, etc.), for example.

Figure 3:
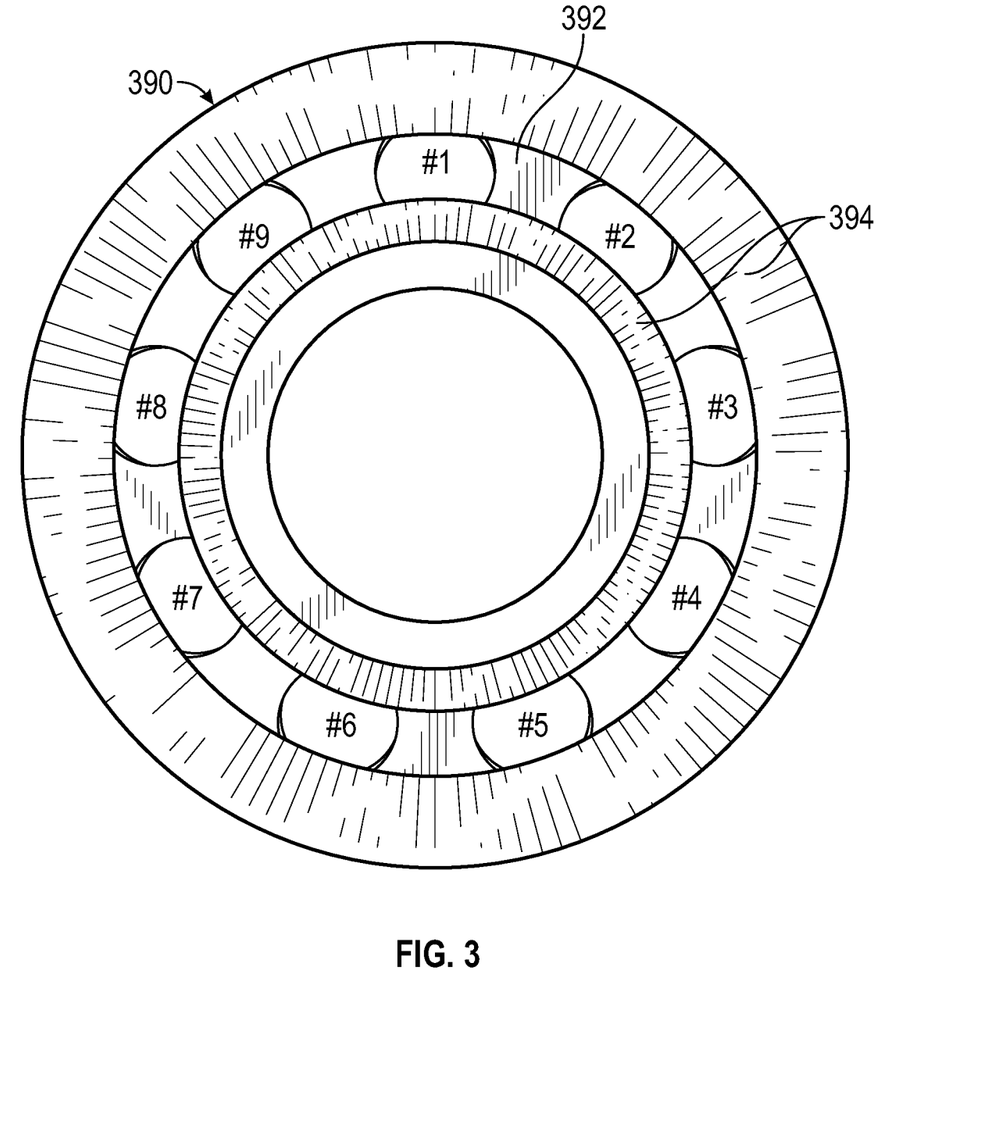
FIG. 3 is an axial view of the combustion chamber of FIG. 1.

The inspection head extender 820 is configured to position or "extend" the inspection head 810 into the combustion chamber 390 (FIG. 3). The inspection head extender 820 may include an extension arm 821 and a roll actuator 822. The inspection head extender 820 may passively extend the inspection head 810 via installation, by the extension arm 821 having a fixed length that reaches into the combustion chamber 390. In addition, portions of the inspection device housing 830 may also be configured to passively extend the inspection head extender 820. For example, the portion of the inner platform 833 beyond landing ridge 837 may extend into combustion chamber 390, further extending the inspection head 810 during the installation process.

Alternately, the inspection head extender 820 may actively extend the inspection head 810 after installation. In particular, the extension arm 821 may be telescopic or otherwise have a variable length, and the inspection head extender 820 may further include an extension actuator (not shown) configured to move the extension arm 821 into and out of the combustion chamber 390.

The extension arm 821 supports and physically extends the inspection head 810 into the combustion chamber 390 during an inspection. In particular, the extension arm 821 positions the inspection head 810 sufficiently into the combustion chamber 390 so as to provide for the inspection data to be collected. According to one embodiment the extension arm 821 may be a rigid member such as a machined rod. Also, the extension arm 821 is supported by the inspection device housing 830. According to one embodiment, the extension arm 821 may be supported so as to rotate in the primary axis.

Where the extension arm 821 is free to rotate in the primary axis, the inspection head extender 820 includes a roll actuator 822. The roll actuator 822 may be an electric motor mechanically coupled to and interspersed between the inspection device housing 830 and the extension arm 821. As illustrated, here the roll actuator 822 is fixed to the inner platform 833 with its rotating shaft (not shown) mechanically coupled to the end of extension arm 821 opposite the camera 811, and the extension arm 821 is supported by two bearing surfaces 834.

The roll actuator 822 is configured to rotate the extension arm 821 about the primary axis 805, and thus provide roll to the camera 811. In particular, the roll actuator 822 may provide the camera 811 with a 360-degree field of view about the primary axis. In addition, the roll actuator 822 may work in coordination with any other actuators of the imaging inspection device 802 to position and orient the camera 811 as needed to perform the inspection of the combustion chamber 390. For example, the roll actuator 822 may work in conjunction with the pitch actuator 813 to provide the camera 811 with a spherical field of view within the combustion chamber 390.

According to one embodiment, the roll actuator 822 may be a stepper motor. In particular, the roll actuator 822 may have a basic step angle of 0.72-degree, for a total of 500 steps per revolution. According to one embodiment, the pitch actuator 813 may be a model CRK543AP stepper motor from Oriental Motor of Torrance, Calif.

According to one embodiment, the inspection head extender 820 may actively extend into the combustion chamber 390 after the imaging inspection device 802 is installed. In particular, the imaging inspection device 802 will have a third degree of freedom. Accordingly, the inspection head extender 820 may further include an extension actuator (not shown) configured to move the extension arm 821 linearly along the primary axis 805. According to one embodiment, the inspection head extender 820 may be a telescopic member, with the extension actuator (not shown) configured to deploy and retract the inspection head extender 820 within the combustion chamber 390.

The inspection device housing 830 is configured to interface with the gas turbine engine and to support the inspection head extender 820. The inspection device housing 830 may also be configured to support additional componentry of the imaging inspection device 802 as a hardware capsule. The inspection device housing 830 may include a combustor interface 831, an outer casing 832, and an inner platform 833.

The combustor interface 831 mechanically couples the inspection device housing 830 to the gas turbine engine. In particular, the combustor interface 831 may include a mounting flange similar to an injector mounting flange. In this way the inspection device housing 830 may be attached to the combustor, for example, through an injector port and in the same or similar manner as an injector. Moreover, the combustor interface 831 may be configured to be installed into an injector port and secured via preexisting attachment features used to secure an injector in the injector port. As used here, the injector port may include any portion or all of where the gas turbine engine interfaces with an injector. For example, the injector may include an interface at the outer casing, an open cavity in the dump region of the diffuser, and/or an injector opening in the combustion chamber.

According to one embodiment the combustor interface 831 may be keyed to prevent rotation. The combustor interface 831 may also be keyed such that it may only be installed in a single orientation. According to one embodiment the combustor interface 831 may include an indexing key 840, the indexing key 840 establishing a location reference or starting reference for the inspection head 810. For example, indexing key 840 may provide a reference to the TDC (top dead center) location of an injector port.

The outer casing 832 includes a structural member mechanically coupled to the combustor interface 831 and traversing the open chamber between the injector port on the outside of the gas turbine engine and the combustion chamber dome 392 (FIG. 4). The outer casing 832 may also include one or more handles 835 to facilitate installation.

According to one embodiment the outer casing 832 forms an enclosure that includes a landing interface and cavity configured to receive the inner platform 833. In particular, the landing interface may slideably receive the inner platform 833. In addition, the landing interface may be configured such that the outer casing may be installed into the injector port without the inner platform 833, and the inner platform 833 is installed afterward, reducing the risk of contact with the inspection head 810 during installation.

The inner platform 833 includes a structural member mechanically coupled to the outer casing 832 and configured to support the inspection head via the inspection head extender 820. In particular, the inner platform 833 may mate with the outer casing 832 such that it may be slid into the outer casing 832 after the outer casing 832 is secured to the combustor the injector port. Additionally, may include interfacing supports configured to receive and support the inspection head extender 820. For example, where the inspection head extender 820 is configured to rotate about the primary axis 805 via the roll actuator 822, the inner platform 833 may include one or more bearing interfaces 834 configured to support the inspection head extender 820 while providing for rotation about the primary axis 805.

The inner platform 833 may include additional features. According to one embodiment, the inner platform 833 may include a tab key 839 or other indexing device configured to index the inner platform 833 to the outer casing 832, which is indexed to the injector port. Here, the tab key 839 may interface with and follow a mating a guide rail or key slot (not shown) cut into the inner surface of the outer casing 832.

According to one embodiment the inner platform 833 may also include one or more handles 835 for engaging the inner platform 833 with, and disengaging it from the outer casing 832. In conjunction with handle 835, the tab key 839 may double as a rotating lock. For example, the inner platform 833 may be engaged with the outer casing 832 by first axially sliding the inner platform 833 into the outer casing 832 (the tab key 839 following a guide rail cut into the outer casing 832), then rotating the handle 835 through a preset angle (positively set by the tab key 839 following a guide rail combination) and continuing to slide the inner platform 833 further into the outer casing 832, then rotating the handle 835 through the reverse of the preset angle to a fully engaged, and locked, position.

According to one embodiment the inner platform 833 may include one or more component mounts 836. In particular, the inner platform 833 may include landing and mounting areas for functional components, and/or for portions of the electronic package to be conveniently installed. For example, the roll actuator 822 may be installed on a component mount 836 on the inner platform 833, with the component mount 836 including an access hole (not shown) concentric with the primary axis 805. In this way, a drive shaft (not shown) of the roll actuator 822 may interface with the inspection head extender 820 and be configured to deliver movement in a rotational direction to the inspection head extender 820. Also for example, circuitry such as motor drivers 838 for the roll actuator 822 and the pitch actuator 813 may be installed locally on the one or more component mounts 836.

With regard to the controller 804, the controller 804 is both a user interface and is configured to control the imaging inspection device 802. As a user interface, the controller 804 includes a first trigger configured to initiate a predefined sequence of inspection head manipulations. In particular, the controller 804 may include one or more program start buttons 861 that start an inspection. For example, as illustrated, the controller 804 may include three program start button 861 where each associated inspection covers a third of the combustion chamber 390. Alternately, each program start button 861 may be associated with an inspection designed for a specific purpose. It is understood that a trigger may be embodied as any convenient user interface configured to initiate the intended action, here being the inspection.

The controller 804 may also include additional triggers and features. In particular, the controller 804 may include additional triggers or user controls over the operational components of the imaging inspection device 802 and/or user feedback media. For example, the controller 804 may include a manual override 862 configured to manually override an inspection in progress. This may be useful where a user discovers a point of interest during the inspection. Also for example, the controller 804 may include an emergency stop 863 configured to terminate an inspection in progress. Also for example, the controller 804 may include a camera display 865 configured to provide real-time images taken by the camera 811.

According to one embodiment, the controller 804 may include a manual controller 864 configured to manipulate the inspection head directly in response to user input. The manual controller 864 may provide camera/video control (e.g., zoom, record, stop), motion control of the inspection head 810, etc. The manual controller 864 may also be tied to a "release" state, such as being prefaced on the activation of an intervening trigger like engagement of the manual override 862.

According to one embodiment, the controller 804 may include an operator user interface model OP300 from Oriental Motor of Torrance, Calif. The main function of the operator user interface model OP300 is to provide information to the inspector. During execution of a program, the operator user interface model OP300 will display a number of steps, which will allow the inspector to quickly confirm that the programs are running as intended. The operator user interface model OP300 also allows for spontaneous control of the motors on the field. Should the inspector find something worth taking a closer look at, he will be able to do so using the operator user interface model OP300. As discussed above, the inspector will be able to interrupt a running motor control program and move the actuators as he desires. This approach is intended as an alternate manner of controlling the inspection head 810.

As a control of the imaging inspection device 802, the controller 804 may include a power supply 866, a processor 867, a memory 868, and a communication device 869. One or more features of the controller 804 may reside on, be shared with, and/or be distributed across the imaging inspection device 802. As illustrated here, the controller 804 (and the imaging inspection device 802) may be powered by the power supply 866, which may include an external power supply, a stored energy supply (i.e., batteries), or a combination thereof. According to one embodiment, the imaging inspection system 800 may be supplied with a 24 VDC power supply and include a step down transformer configured to supply 12 VDC to components such as the light source 812.

The processor 867 and the memory 868 work together to implement the functionality of the imaging inspection system 800. The processor 867 may include one or more processors and the memory 868 may include one or more memory devices. According to one embodiment, the memory 868 can be integral to the processor 867. For example, the processor 867 and the storage medium can reside in an ASIC.

The processor 867 may be configured to issue commands to one or more components of the imaging inspection device 802. In particular, the processor 867 may issue commands directing a automated/predefined sequence of manipulations of the inspection head 810 including maneuvering and operating the camera 811 along a predetermined path.

According to one embodiment, the processor 867 may include an EMP402-2 Motor Controller from Oriental Motor of Torrance, Calif. to control the pitch actuator 813 and the roll actuator 822. The EMP402-2 is able to control two different motors simultaneously, and can store up to 32 different programs, with a combined maximum of 1000 program lines. The EMP402-2 is also compatible with the OP300 Operator User Interface. The EMP402-2 requires a 24 VDC power source. Programs for the EMP402-2 may be written to the memory 868 using Windows Hyperterminal, a standard Windows Program Accessory.

The memory 868 may be embodied as RAM memory, flash memory, ROM memory, EPROM memory, EEPROM memory, registers, hard disk, a removable disk, a CD-ROM, video tape and/or any other form of machine or computer readable storage medium. The memory 868 may include a control module 871 and an imagery module 872. The control module 871 may be programmed or otherwise configured to store instructions for a predefined sequence of inspection head manipulations. The imagery module 872 may be configured to record imagery (e.g., video) or other data received from one or more components of the inspection head 810.

An exemplary storage medium can be coupled to the processor 867 such that the processor 867 can read information from, and write information to, the storage medium. According to one embodiment, memory 868 is configured to record instructions for a sequence of movements of the inspection head defining the predetermined path. According to one embodiment, the controller 804 is configured to record video of the combustion chamber 390 along a predetermined path onto the memory 868.

The controller 804 (and the imaging inspection device 802) may include a communication device 869. The communication device may reside on the controller 804, on the imaging inspection device 802, or a combination thereof. The communication device 869 is configured to communicate commands from the controller 804 and data from the inspection head 810.

According to one embodiment, the communication device 869 may include a wireless transceiver communicably coupled to the controller 804 and configured to receive inspection data, for example from the camera 811, and transmit commands from the controller 804. According to one embodiment, the communication device 869 may be further configured to communicate with devices outside of the controller 804 and the imaging inspection device 802 using wired or wireless means. According to one embodiment, the communication device 869 includes a tether or wired connection, which may provide for both communications and power between the imaging inspection device 802 and the controller 804.

FIG. 3 is an axial view of the combustion chamber of FIG. 1. In particular, this view is looking forward (upstream) into combustion chamber 390 with the combustion chamber dome 392 at the far side and the exit cone 394 at the near side. Also, as illustrated, the combustion chamber dome 392 includes nine injector openings 395, conveniently numbered consecutively in the clockwise direction. The illustrated numbering convention is for convenience only and may vary from application to application.

According to one embodiment, the presently disclosed imaging inspection system may be programmed to inspect the combustion chamber 390 quickly and efficiently. In particular, the imaging inspection system may be programmed to inspect the entire liner by only being installed in three injector ports. For example, using the illustrated numbering convention, the imaging inspection device may be installed in injector port #1, #4, and #7. These particular injector ports are representative only, as other injector ports may be used instead, in combination, or in addition to those identified. Moreover, selection of the injector ports or the number thereof may also turn on port accessibility, actual view range, and/or other considerations.

FIG. 4 is partial cutaway view of a 180-degree injector installed in a combustion chamber of a gas turbine engine. In particular, injector 351 is shown installed in combustor 301 through the aft end of diffuser 321 and into an injector opening 395 of combustion chamber 390. Unlike the injector 350 of FIG. 1 (a 90-degree injector), injector 351 enters the combustion chamber 390 at a 180-degree angle (or in a straight line along primary axis 805). Within the combustion chamber 390 is the combustion region 391. The combustion region 391 is partially bounded by the liner, which includes the combustion chamber dome 392, the combustion chamber walls 393, and the exit cone 394.

The imaging inspection device described above may be installed into injector opening 395 to inspect the inner surfaces of the combustion chamber 390. In particular, the imaging inspection device may be installed via an injector port of the diffuser 321 to an injector opening 395 of combustion chamber 390, replacing an injector. Once installed, an automated inspection may be conducted to search for defects, spallation, cracks in the TBC, distortion of sheet metal, oxidation or thermal distress, proper fit up of components (e.g., ignition torch), engagement of any adjacent injectors 351, and/or distress in any visible components outside of the exit cone 394 (e.g., components in the first stage of the turbine).

Those of skill will appreciate that the various illustrative modules, units, logical blocks, and algorithm steps described in connection with the embodiments disclosed herein can often be implemented as electronic hardware, computer software, or combinations of both. To clearly illustrate this interchangeability of hardware and software, various illustrative components, units, blocks, modules, and steps have been described above generally in terms of their functionality. Whether such functionality is implemented as hardware or software depends upon the particular system and design constraints imposed on the overall system Skilled persons can implement the described functionality in varying ways for each particular system, but such implementation decisions should not be interpreted as causing a departure from the scope of the invention. In addition, the grouping of functions within a unit, module, block, or step is for ease of description. Specific functions or steps can be moved from one unit, module, or block without departing from the invention.

The various illustrative logical blocks, units, steps and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, or microcontroller. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm and the processes of a block or module described in connection with the embodiments disclosed herein can be embodied directly in hardware, in a software module (or unit) executed by a processor, or in a combination of the two. A software module can reside in the memory.

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Industrial Applicability

The present disclosure generally applies to an imaging inspection system, and inspection of the interior of a gas turbine combustor chamber including its surfaces and mating/interfacing components such as injectors and torches. The described embodiments are not limited to use in conjunction with a particular type of gas turbine engine, but rather may be applied to stationary or motive gas turbine engines, or any variant thereof. Gas turbine engines, and thus their components, may be suited for any number of industrial applications, such as, but not limited to, various aspects of the oil and natural gas industry (including include transmission, gathering, storage, withdrawal, and lifting of oil and natural gas), power generation industry, aerospace and transportation industry, to name a few examples.

Generally, embodiments of the presently disclosed imaging inspection system are applicable to the use, operation, maintenance, repair, and improvement of gas turbine engines, and may be used in order to improve performance and efficiency, decrease maintenance and repair, and/or lower costs. In addition, embodiments of the presently disclosed imaging inspection system may be applicable at any stage of the gas turbine engine's life, from design to prototyping and first manufacture, and onward to end of life. The disclosed imaging inspection system may be used for inspection of the gas turbine engine's health and the diagnosis of problems. Accordingly, the imaging inspection system may be used in conjunction with a retrofit or enhancement to existing gas turbine engine, as a preventative measure, or even in response to an event.

In particular, the presently disclosed imaging inspection system may reduce time and costs associated with earlier types of combustion chamber inspection devices. Moreover the presently disclosed imaging inspection system may provide for greater consistency in inspections and higher quality data recovery and review than with earlier types of combustion chamber inspections. The presently disclosed imaging inspection system is particularly beneficial as inspections using older inspection techniques lacked the referencing, precision, and repeatability provided here. For example, while area of interest may be discovered using an older techinque, additional inquiry may be required to located where the image was taken. In contrast, a technician may merely install the presently disclosed imaging inspection system and initiate the inspection, and comprehensive inspection information may be created for evaluation by a specialist located remotely from the gas turbine engine.

Figure 5:
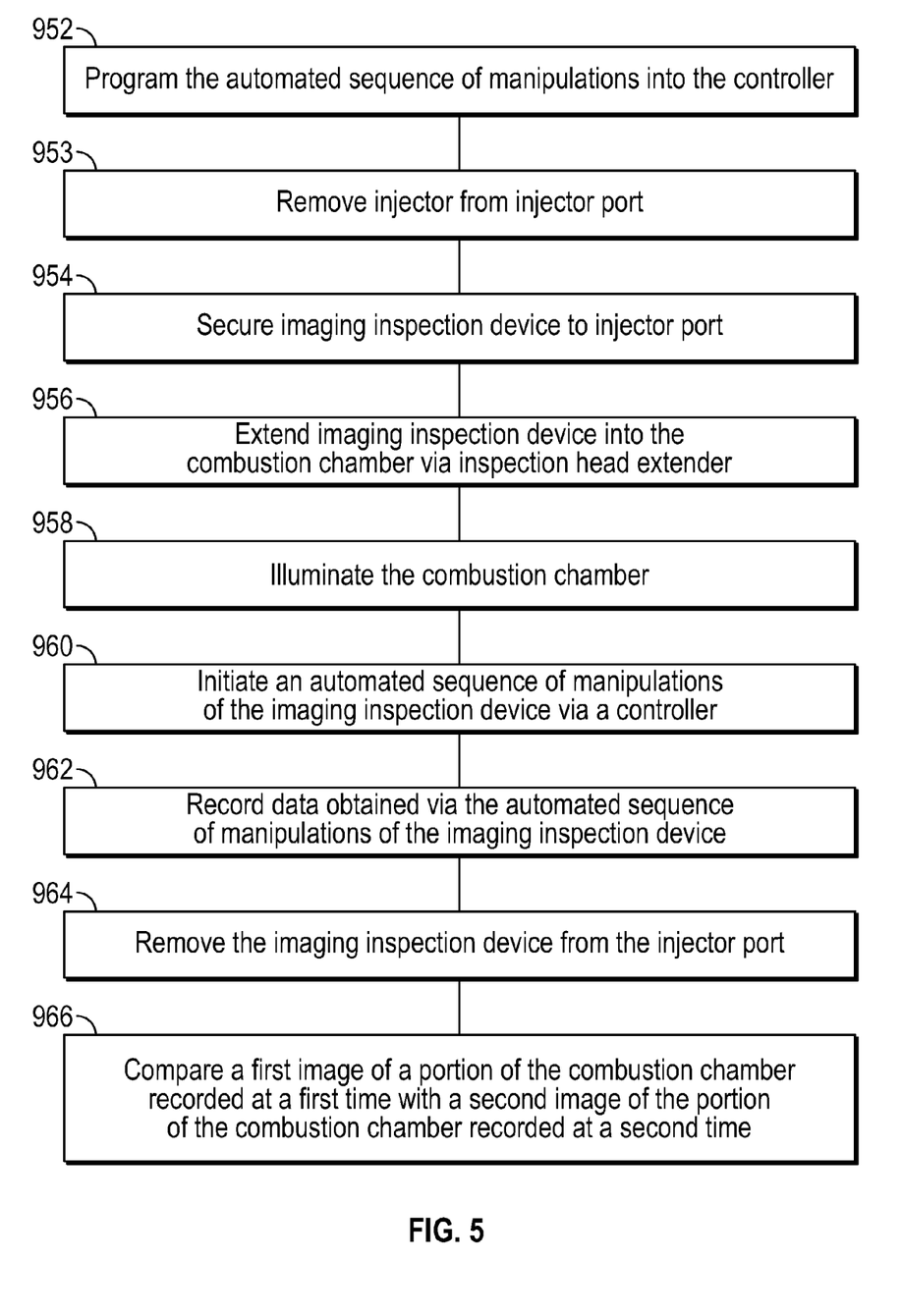
FIG. 5 is a flow chart of an exemplary method for inspecting a combustion chamber of a gas turbine engine.

FIG. 5 is a flow chart of an exemplary method for inspecting a combustion chamber of a gas turbine engine. In particular, the method corresponds to inspecting the combustion chamber of a gas turbine engine with a programmable imaging inspection device.

Optionally, according to one embodiment, the method may include programming the automated sequence of manipulations into the controller 952. Programming may include, selecting from a library of programs, tailoring an existing general program to the parameters of the specific combustion chamber, modifying an existing program, and/or creating an original program to include the automated sequence of manipulations of the imaging inspection device. Programming may be performed via a computer and computer interface or communication device. Where equipped with the appropriate user interface, the automated sequence of manipulations may be programmed directly to a memory of the controller.

The method generally includes the steps of removing an injector from an injector port 953, securing an imaging inspection device to an injector port 954, initiating an automated sequence of manipulations of the imaging inspection device via a controller 960, recording data obtained via the automated sequence of manipulations of the imaging inspection device 962, and removing the imaging inspection device from the injector port 964.

The automated sequence of manipulations may include movements of one or more components of the imaging inspection device (e.g., camera, light source, extension arm, etc.). The automated sequence of manipulations may include state changes as well (e.g., camera on/of, light source on/of, sensor on/off, etc.). According to one embodiment, the automated sequence of manipulations of the imaging inspection device may include a starting reference. The starting reference coordinates the imaging inspection device with the area to be inspected. The starting reference may be determined via an indexing feature such as a indexing key, an identified starting orientation/position, a recognition of a known feature, and/or any other coordination between the imaging inspection system and the inspected area.

According to one embodiment, the automated sequence of manipulations of the imaging inspection device may include rotating the camera about the primary axis via the roll actuator, and pitching the camera about an axis perpendicular to the primary axis via the pitch actuator. According to another embodiment, the imaging inspection device includes an inspection head with a proximity sensor, the automated sequence of manipulations of the imaging inspection device may include measuring the locations of points on an inner wall of the combustion chamber such that distortion may be measured and/or a 3-D map may be constructed using the recorded data obtained via the automated sequence of manipulations of the imaging inspection device.

In conjunction with the above descriptions, securing an imaging inspection device to an injector port 954 may include mounting or installing the imaging inspection device in a similar manner as installing an injector. The imaging inspection device is designed to work in place of a removed gas injector, so upon removal of an injector, a user or inspector installs the imaging inspection device in its place. Accordingly, securing the imaging inspection device to the injector port may be performed using preexisting attachment features configured to attach an injector, such as bolting the imaging inspection device to an injector flange receiver.

Installing the imaging inspection device in the injector's place may also include aligning one or more indexing features. In particular, securing the imaging inspection device to the injector port may include indexing the imaging inspection device to combustion chamber so as to establish a known starting reference for the imaging inspection device. Also, where there is a two-part inspection device housing (as discussed above), the inspector first installs the outer casing of the imaging inspection device in place, then the inspector may further install the inner platform. Both installations (inner and outer) may include indexing, alignment, and locking features.

The method may further include extending the imaging inspection device into the combustion chamber via the inspection head extender 956. Where the imaging inspection device includes a fixed length inspection head extender, inserting the inner platform into the outer casing of the imaging inspection device may also extend the camera approximately 4.5 inches (11.43 cm) into the combustion chamber. Providing viewing access to the combustor dome, the combustor walls, and the exit cone. Alternately, where the imaging inspection device includes a variable length inspection head extender, extending the imaging inspection device into the combustion chamber may include operating an extension actuator, which may be included as part of the above automated sequence of manipulations.

The method may further include illuminating the combustion chamber 958. In particular, a light source may be activated on the imaging inspection device. For example, the inspector may manually activate the light source, and/or the light source may be automatically activated via the automated sequence of manipulations. According to one embodiment, the method may further include lighting the combustion chamber with indirect light, relative to the camera, via the light source. For example, the light source may be located remotely from the inspection head, such as on the end of the inner platform or on the extension arm. Where the light source is located on the inspection head, the light source may be pointed in a different direction than the camera, or otherwise diffused.

Also, in conjunction with the above descriptions, initiating an automated sequence of manipulations of the imaging inspection device via a controller 960 may include initiating a programmed/predefined sequence of inspection head manipulations using a first trigger, which may include a simple start button or any other convenient trigger. For example, after installing the imaging inspection device, a "start" switch can be turned on to begin the inspection. After the inspection has begun, an indicator such as a "RUN" LED may light up showing that the program is in progress.

Also, in conjunction with the above descriptions, recording data obtained via the automated sequence of manipulations of the imaging inspection device 962 may include recording data such as video and/or other imagery to a memory of the imaging inspection system. Additional data may be recorded as well, such as position data from actuators, sensor data, etc.

The inspector will have access to the controller, where he may use previously created programs to aim the inspection head throughout the combustion chamber as programmed. The programs include the automated sequence of manipulations of the imaging inspection device, but may also be modified real-time. In particular, the programs may be overridden, redefined, terminated, and/or re-initiated.

According to one embodiment, in addition to performing the basic programs provided, the inspector may have the capability to "customize" an imaging inspection as deemed fit in real-time. For example, where an existing program is insufficient, the examiner may revise the program or create a new program altogether. Also for example, if there is a problem, an emergency stop may be activated. Also for example, where there is an area of interest (e.g., on the camera display), the inspector may engage a manual override and directly operate the imaging inspection device via a manual controller. Also for example, where an inspection sequence does not run properly, the method may be restarted. To restart the method, the first trigger may be used again to initiate the programmed sequence of inspection head manipulations.

Also, in conjunction with the above descriptions, removing the imaging inspection device from the injector port 964 may be the reverse of installation. In particular, the imaging inspection device may be removed the injector port in the reverse of securing it to the injector port. Moreover, removing the imaging inspection device may also include reinstallation of any removed components (e.g., one or more injectors removed).

According to one embodiment, the method may include inspecting an area of the combustion chamber beyond that of an area proximate a single injector port. In particular, a complete inspection of a combustion chamber may include securing imaging inspection device to fewer that all of its injector ports. For example, where the combustion chamber of the gas turbine engine includes an annular liner, the automated sequence of manipulations of the imaging inspection device may include collecting imagery of at least one third of the annular liner. In this way the method is then repeated with two more injector ports.

By accessing three roughly equidistant ports, a general mapping of the combustor dome may be possible. This may efficiently accomplish the required task of determining the overall health of the combustion dome lining. Combined with the automation, a single automated sequence of manipulations may be performed in no longer than approximately 5-10 minutes after being initiated. It is understood, that different combustion chamber geometries and configurations may require a greater number of applications of the method. For example, a complete inspection of a combustion chamber may require applying the method to four injector ports instead of three.

Once the imagery has been taken, it may be stored or arranged in a manner suited for further analysis. In particular, the imagery may be compared against a reference such as a starting reference described above. For example the method may include comparing a first image of a portion of the combustion chamber recorded at a first time with a second image of the same portion of the combustion chamber recorded at a second time 966. This is beneficial as it provides for an age progression analysis and other longitudinal studies. Throughout the inspection, an inspector may "tag" the video or otherwise identify a point of interest during the inspection. As discussed above the imagery taken may be stored in a statistical format for analysis and/or visually arranged as a map (e.g., 3-D, ocular, etc.) for further analysis by the inspector or other users.

Embodiments of the presently disclosed combustor imaging inspection system and method of use provide for an efficient and repeatable inspection of a combustion chamber in a gas turbine engine. In particular, the system and method provide for an inspector to easily place the inspection device into the turbine, provides for allowing programs to perform the majority of the inspection, while still allowing the inspector a way to override should it be necessary. The system and method provide for consistent, high quality inspections, as there is no dependence on the inspector's hand dexterity. The system and method provide for ease of use as inspector need only pay attention to the execution of the inspection and "tag" the video at important moments. The system and method may further provide for an entire combustion chamber inspection being performed in less than 1.5 hours. Also, the system and method provide inspection data that is consistent, and always from the same angles and distances.

The preceding detailed description is merely exemplary in nature and is not intended to limit the invention or the application and uses of the invention. The described embodiments are not limited to use in conjunction with a particular type of gas turbine engine. Hence, although the present embodiments are, for convenience of explanation, depicted and described as being implemented in a stationary gas turbine engine, it will be appreciated that it can be implemented in various other types of gas turbine engines, and in various other systems and environments. Furthermore, there is no intention to be bound by any theory presented in any preceding section. It is also understood that the illustrations may include exaggerated dimensions and graphical representation to better illustrate the referenced items shown, and are not consider limiting unless expressly stated as such.

What is claimed is:

1. An imaging inspection system for a combustion chamber of a gas turbine engine, the imaging inspection system comprising:
    a combustor interface configured to secure at least a portion of the imaging inspection system to a combustor of the gas turbine engine;
    an inspection head including a first camera;
    an inspection head extender, the inspection head extender mechanically coupled to the combustor interface and to the inspection head, the inspection head extender configured to position the inspection head into the combustion chamber;
    a first actuator configured to move a view of the first camera in a first direction;
    a second actuator configured to move the view of the first camera in a second direction different from the first direction;
    a controller configured to control the first actuator and the second actuator to manipulate the inspection head in a predefined sequence;
    an inner platform configured to support the inspection head extender; and
    an outer casing comprising a structural member mechanically coupled to the combustor interface, and configured to traverse an open chamber between an injector port on the outside of the gas turbine engine and a combustion chamber dome, the outer casing further configured to receive and support the inner platform, the outer casing further configured to be installed into the injector port with or without the inner platform.

2. The imaging inspection system of claim 1, further comprising an indexing key, the indexing key establishing the starting reference, the starting reference including a location reference for the imaging inspection system relative to the combustion chamber to be inspected.

3. The imaging inspection system of claim 1, wherein the inspection head further includes a second camera.

4. The imaging inspection system of claim 1, wherein the inspection head further includes a proximity sensor.

5. The imaging inspection system of claim 1, wherein the controller includes a user interface, the user interface including
    a first trigger configured to initiate the predefined sequence of inspection head manipulations,
    a second trigger configured to manually override to the predefined sequence of inspection head manipulations,
    a third trigger configured stop to the predefined sequence of inspection head manipulations,
    a display configured to provide real-time images taken by the first camera, and
    one or more user controls configured to manually manipulate the inspection head.

6. The imaging inspection system of claim 1, wherein the controller includes a processor and a memory;
    wherein the predefined sequence of manipulations of the inspection head include maneuvering and operating the first camera along a predetermined path via commands from the processor; and
    wherein the controller is configured to record video of the combustion chamber along the predetermined path.

7. The imaging inspection system of claim 1, further comprising a wireless transceiver communicably coupled to the controller, the wireless transceiver configured to receive data from the first camera and transmit commands from the controller.

8. An imaging inspection system for a combustion chamber of a gas turbine engine, the imaging inspection system comprising:
    an inspection head including a first camera;
    an inspection head extender mechanically coupled to the inspection head, the inspection head extender indexed to a reference on the combustion chamber;
    a first actuator configured to move a view of the first camera in a first direction;
    a second actuator configured to move the view of the first camera in a second direction different from the first direction;
    a processor and a control module configured together to issue commands to operate the first camera and to cause the first actuator and the second actuator to move the inspection head according to a predetermined path, the control module being programmed to store instructions for a predefined sequence of the inspection head manipulations defining the predetermined path;

a memory configured to host the control module and a imagery module, the imagery module configured to record imagery received from the first camera; and a first trigger configured to initiate the predefined sequence of the inspection head manipulations.

9. The imaging inspection system of claim 8, wherein the first camera is a video camera; and wherein the inspection head further includes a second camera and a proximity sensor.

10. The imaging inspection system of claim 8, further comprising an inspection device housing, the inspection device housing including a combustor interface, an inner platform, and an outer casing, the combustor interface configured to mount to an injector port, the inner platform configured to support the inspection head, the outer casing configured to receive and support the inner platform; and wherein the first actuator includes a roll actuator; and wherein the second actuator includes a pitch actuator.

11. The imaging inspection system of claim 10, wherein the inspection head extender has a fixed length and is configured to support the inspection head at the fixed length within the combustion chamber; and wherein the inspection head extender is supported by the inner platform;

wherein the inner platform is configured to support the inspection head via the inspection head extender; and wherein the first camera is configured to vary its focal distance.

12. A method for inspecting a combustion chamber for a combustor of a gas turbine engine with an imaging inspection system including a combustion interface, an inspection head, an inspection head extender, a first actuator, a second actuator, and a controller having a first trigger, the method comprising:

removing an injector from an injector port of the combustor;

installing at least a portion of the imaging inspection system into the injector port;

securing at least the portion of the imaging inspection system to the injector port-using the combustor interface;

positioning the inspection head including a first camera into the combustion chamber using the inspection head extender, the inspection head extender being mechanically coupled to the combustor interface and to the inspection head;

performing an automated sequence of manipulations of the inspection head by directing the first actuator to move a view of the first camera in a first direction with the controller and by directing the second actuator to move a view of the first camera in a second direction with the controller, the second direction being different from the first direction;

initiating the automated sequence of manipulations of the inspection head with the first trigger;

recording data obtained via the automated sequence of manipulations of the inspection head; and removing the inspection head from the combustion chamber and detaching the portion of the imaging inspection head secured to the injector port.

13. The method of claim 12, wherein securing the portion of the imaging inspection system to the injector port includes indexing the inspection head to the combustion chamber so as to establish the starting reference for the inspection head.

14. The method of claim 12, wherein the first actuator is a roll actuator and the second actuator is a pitch actuator and performing the automated sequence of manipulations of the inspection head includes rotating the camera about a primary axis via the first actuator, and pitching the camera about an axis perpendicular to the primary axis via the second actuator.

15. The method of claim 12, wherein the imaging inspection system includes a light source; and wherein the method further comprises lighting the combustion chamber with indirect light relative to the camera via the light source.

16. The method of claim 12, wherein the combustion chamber includes an annular liner; and wherein performing the automated sequence of manipulations of the inspection head includes collecting imagery of approximately one third of the annular liner.

17. The method of claim 12, wherein the inspection head includes a proximity sensor; and wherein performing the automated sequence of manipulations of the inspection head includes measuring the locations of points on an inner wall of the combustion chamber with the proximity sensor such that distortion may be measured and/or a 3-D map may be constructed using the recorded data obtained.

18. The method of claim 12, further comprising comparing a first image of a portion of the combustion chamber recorded at a first time with a second image of the portion of the combustion chamber recorded at a second time.

19. The method of claim 12, wherein the controller is programmed to store instructions defining a predetermined path for the automated sequence of manipulations of the inspection head.

* * * * *